United States Patent
Torigoe et al.

(10) Patent No.: US 6,207,641 B1
(45) Date of Patent: *Mar. 27, 2001

(54) PHARMACEUTICAL COMPOSITION CONTAINING IFN-γ INDUCING POLYPEPTIDE OR FACTOR FOR TREATING AND/OR PREVENTING IFN-γ SUSCEPTIVE DISEASES

(75) Inventors: Kakuji Torigoe; Tadao Tanimoto; Shigeharu Fukuda; Masashi Kurimoto, all of Okayama (JP)

(73) Assignee: Kabushiki Kaisha Hayashibara Seibutsu Kagaku Kenkyujo, Okayama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/974,469

(22) Filed: Nov. 20, 1997

Related U.S. Application Data

(63) Continuation of application No. 08/599,879, filed on Feb. 14, 1996, now abandoned, which is a continuation-in-part of application No. 08/558,190, filed on Nov. 15, 1995, now abandoned.

(30) Foreign Application Priority Data

Mar. 10, 1995 (JP) ................................... 7-078357
Sep. 29, 1995 (JP) ................................... 7-274988

(51) Int. Cl.$^7$ .......................... A61K 38/17; C07K 14/00
(52) U.S. Cl. .................... 514/12; 514/21; 514/2; 530/351; 530/350; 530/324

(58) Field of Search ..................... 514/12, 21, 2; 530/351, 350, 324

(56) References Cited

U.S. PATENT DOCUMENTS

| | | | | |
|---|---|---|---|---|
| 4,645,830 | * | 2/1987 | Yasushi et al. | 530/351 |
| 4,803,072 | * | 2/1989 | Dalton et al. | 424/85.5 |
| 4,908,432 | * | 3/1990 | Yip | 530/351 |
| 5,147,638 | * | 9/1992 | Esmon et al. | 424/85.8 |
| 5,218,096 | * | 6/1993 | Shibuya et al. | 536/41 |

OTHER PUBLICATIONS

Okamura et al, Nature, vol. 378, pp. 88–91, (Nov. 2, 1995).*
Okamura et al, Infection and Immunity, vol. 63(10), pp. 3966–3972, (Oct. 1995).*
Nakamura et al, Infection and Immunity, vol. 61(1), pp. 64–70, (Jan. 1993).*
Balkwill, Frances, R., Cytokines in Cancer Therapy, pp. 1–237, (1989).
Fujioka, T. et al. "Combination of Lympokine–Activated Killer Cells and Interleukin–2 in Treating Metastatic Renal Cell Carcinoma", British Journal of Urology, vol. 73, pp. 23–31 (1994).

* cited by examiner

*Primary Examiner*—T. D. Wessendorf
(74) *Attorney, Agent, or Firm*—Browdy And Neimark

(57) ABSTRACT

An agent for susceptive diseases, which contains a polypeptide that has a molecular weight of 18,500±3,000 daltons on SDS-PAGE and a pI of 4.9±1.0 on chromatofocusing, strongly induces the IFN-γ production by immunocompetent cells with only a small amount, and does not cause serious side effects even when administered to human at a relatively-high dose. The agent treats and/or prevents malignant tumors, viral diseases, bacterial infectious diseases, and immune diseases including atopies.

9 Claims, 1 Drawing Sheet

Figure 1:
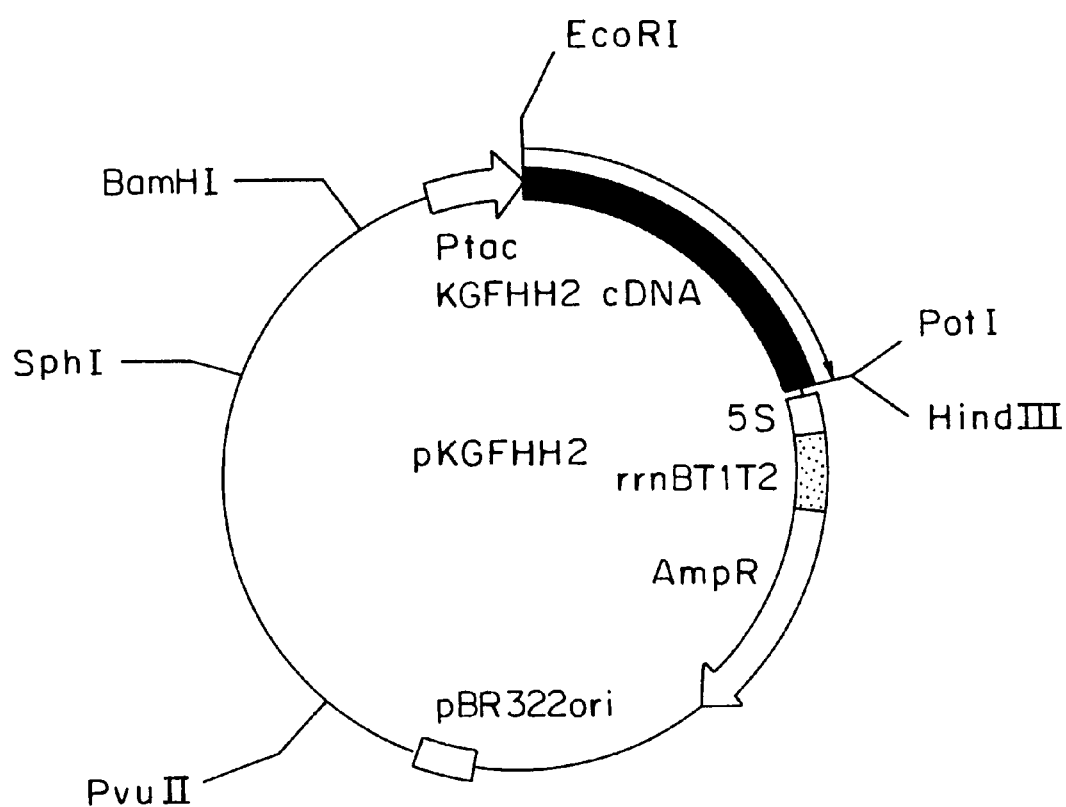

PHARMACEUTICAL COMPOSITION CONTAINING IFN-γ INDUCING POLYPEPTIDE OR FACTOR FOR TREATING AND/OR PREVENTING IFN-γ SUSCEPTIVE DISEASES

CROSS REFERENCE TO RELATED APPLICATION

This application is a continuation of application Ser. No. 08/599,879, filed Feb. 14, 1996, now abandoned, which is a continuation-in-part of Ser. No. 08/558,190, filed Nov. 15, 1995 now abandoned, which application is incorporated hereby by reference in the entirety.

BACKGROUND OF THE INVENTION

1. Field of the Invention

The present invention relates to an agent for susceptive diseases which contains as an effective ingredient a novel polypeptide that induces the interferon-γ (hereinafter abbreviated as "IFN-γ") production by immunocompetent cells.

2. Description of the Prior Art

It is known that IFN-γ is a protein which has antiviral-, antioncotic- and immunoregulatory-activities, and which is produced by immunocompetent cells stimulated with antigens or mitogens. Because of these biological activities, IFN-γ was expected to be used as an antitumor agent since its discovery, and is studied energetically in clinical trials as a therapeutic agent for malignant tumors in general, including brain tumors. Commercially available IFN-γ preparations are roughly classified into two groups, i.e. a group of natural IFN-γs produced by immunocompetent cells and a group of recombinant IFN-γs produced by transformants, obtained by introducing into microorganisms of the species *Escherichia coli* DNAs which encode the natural IFN-γs. In the above clinical trials, one of these two groups of IFN-γs is administered to patients as an "exogenous IFN-γ".

Among these IFN-γs, natural IFN-γs are usually produced by culturing established immunocompetent cells in nutrient culture media supplemented with IFN-γ inducers to form IFN-γs, and purifying the formed IFN-γs. It is known that the type of IFN-γ inducers greatly influences the IFN-γ yield, as well as on the ease of IFN-γ purification and the safety of the final IFN-γ containing products. Generally, mitogens such as concanavalin A (Con A), *Lens culinaris, Phytolacca americana,* endotoxin and lipopolysaccharide can be used as an IFN-γ inducer. However, these mitogens have the problems of molecular varieties and quality changes depending on their origins and purification methods, as well as the difficulties in obtaining preparations having a constant IFN-γ inducibility in a desired amount. In addition, most of these mitogens might induce unfavorable side effects when administered to living bodies, and some of them may even cause toxicity, so that it is substantially difficult to induce the IFN-γ production by directly administering IFN-γ inducers to living bodies.

Recently, some pharmaceuticals, which contain as an effective ingredient cytokines such as interferon-α, interferon-β, TNF-α, TNF-β, interleukin 2, and interleukin 12, as well as IFN-γ, were developed or are being explored for actual use. These pharmaceuticals can be used as an antitumor agent, antiviral agent, antiseptic or immunoregulatory agent and, if necessary, they can be used together with other medicaments.

Unlike chemically synthesized pharmaceuticals, the aforesaid pharmaceuticals have as the greatest feature the characteristic that they can be administered to patients for a relatively-long period of time without inducing serious side effects, but they also have the demerits that their therapeutic effects are generally relatively-low, and they could not substantially remit and cure diseases when used alone, with the results varying depending on the types of diseases and symptoms to be treated. Therefore, these pharmaceuticals are now used as a supplemental agent for chemically synthesized agents in the treatment of serious diseases such as malignant tumors or used to prolong the patients' life.

SUMMARY OF THE INVENTION

In view of the foregoing, the object of the present invention is to provide a pharmaceutical which exerts a strong effect and which can be administered to patients for a relatively long period of time without inducing serious side effects.

The object of the present invention is attained by an agent for susceptive diseases which contains as an effective ingredient a polypeptide having either the amino acid sequence of SEQ ID NO:1 (where the symbol "Xaa" represents "isoleucine" or "threonine") or its homologous amino acid sequence, and inducing the IFN-γ production by immunocompetent cells.

SEQ ID NO:1:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile

```
                              -continued
           35                      40                       45

Ile Ser Met Tyr Lys Asp Ser Gln Pro Arg Gly Met Ala Val Thr Ile
     50                      55                      60

Ser Val Lys Cys Glu Lys Ile Ser Xaa Leu Ser Cys Glu Asn Lys Ile
65                       70                      75                      80

Ile Ser Phe Lys Glu Met Asn Pro Pro Asp Asn Ile Lys Asp Thr Lys
                 85                      90                      95

Ser Asp Ile Ile Phe Phe Gln Arg Ser Val Pro Gly His Asp Asn Lys
            100                     105                     110

Met Gln Phe Glu Ser Ser Ser Tyr Glu Gly Tyr Phe Leu Ala Cys Glu
        115                     120                     125

Lys Glu Arg Asp Leu Phe Lys Leu Ile Leu Lys Lys Glu Asp Glu Leu
    130                     135                     140

Gly Asp Arg Ser Ile Met Phe Thr Val Gln Asn Glu Asp
145                 150                     155
```

The present invention was made based on the finding of a novel polypeptide which induces the IFN-γ production by immunocompetent cells. The present inventors studied cytokines produced from mammalian cells and have found that there exists an IFN-γ production inducing substance in mouse liver which was previously treated with a lipopolysaccharide and inactivated whole cells of Corynebacterium. They isolated the substance by a variety of purification methods using column chromatography as a main technique, studied the properties and features, and have found that this substance is a protein having the following physicochemical properties of:

(1) Molecular weight 19,000±5,000 daltons on sodium dodecyl polyacrylamide gel electrophoresis (SDS-PAGE);
(2) Isoelectric point (pI) pI of 4.8±1.0 on chromatofocusing;
(3) Partial amino acid sequence Having the partial amino acid sequences of SEQ ID NOs:4 and 5; and
(4) Biological activity Inducing the IFN-γ production by immunocompetent cells:

```
SEQ ID NO:4:

Ile Ile Ser Phe Glu Glu Met Asp Pro Pro Glu Asn Ile Asp Asp
                 5                      10                     15

Ile Gln Ser Asp Leu Ile Phe Phe Gln Lys
                20                      25

SEQ ID NO:5:

Gln Pro Val Phe Glu Asp Met Thr Asp Ile Asp Gln Ser Ala Ser Glu
1               5                      10                     15

Pro Gln
```

This data demonstrated that the substance is novel because no protein with such physicochemical properties is known. The present inventors continued their studies on mouse liver cells and have succeeded in isolating a DNA sequence which encodes the protein. They decoded the DNA (SEQ ID NO:6) presented below and have found that it consists of 471 base pairs and encodes the amino acid sequence of SEQ ID NO:7 as presented in parallel immediately below the base of sequence of SEQ ID NO:6.

SEQ ID NO:6:

```
AAC TTT GGC CGA CTT CAC TGT ACA ACC GCA GTA ATA CGG AAT ATA AAT      48
Asn Phe Gly Arg Leu His Cys Thr Thr Ala Val Ile Arg Asn Ile Asn
1                 5                  10                  15

GAC CAA GTT CTC TTC GTT GAC AAA AGA CAG CCT GTG TTC GAG GAT ATG      96
Asp Gln Val Leu Phe Val Asp Lys Arg Gln Pro Val Phe Glu Asp Met
                20                  25                  30

ACT GAT ATT GAT CAA AGT GCC AGT GAA CCC CAG ACC AGA CTG ATA ATA     144
Thr Asp Ile Asp Gln Ser Ala Ser Glu Pro Gln Thr Arg Leu Ile Ile
            35                  40                  45

TAC ATG TAC AAA GAC AGT GAA GTA AGA GGA CTG GCT GTG ACC CTC TCT     192
Tyr Met Tyr Lys Asp Ser Glu Val Arg Gly Leu Ala Val Thr Leu Ser
        50                  55                  60

GTG AAG GAT AGT AAA AYG TCT ACC CTC TCC TGT AAG AAC AAG ATC ATT     240
Val Lys Asp Ser Lys Xaa Ser Thr Leu Ser Cys Lys Asn Lys Ile Ile
65                  70                  75                  80

TCC TTT GAG GAA ATG GAT CCA CCT GAA AAT ATT GAT GAT ATA CAA AGT     288
Ser Phe Glu Glu Met Asp Pro Pro Glu Asn Ile Asp Asp Ile Gln Ser
                85                  90                  95

GAT CTC ATA TTC TTT CAG AAA CGT GTT CCA GGA CAC AAC AAG ATG GAG     336
Asp Leu Ile Phe Phe Gln Lys Arg Val Pro Gly His Asn Lys Met Glu
            100                 105                 110

TTT GAA TCT TCA CTG TAT GAA GGA CAC TTT CTT GCT TGC CAA AAG GAA     384
Phe Glu Ser Ser Leu Tyr Glu Gly His Phe Leu Ala Cys Gln Lys Glu
        115                 120                 125

GAT GAT GCT TTC AAA CTC ATT CTG AAA AAA AAG GAT GAA AAT GGG GAT     432
Asp Asp Ala Phe Lys Leu Ile Leu Lys Lys Lys Asp Glu Asn Gly Asp
    130                 135                 140

AAA TCT GTA ATG TTC ACT CTC ACT AAC TTA CAT CAA AGT                 471
Lys Ser Val Met Phe Thr Leu Thr Asn Leu His Gln Ser
145             150                 155
```

Based on these findings, the present inventors further continued their studies on human liver cells in order to obtain a DNA which encodes another novel substance that induces the IFN-γ production by immunocompetent cells. They revealed that the substance is a polypeptide, and they decoded its DNA, and found that the polypeptide has the amino acid sequence of SEQ ID NO:1. They introduced the DNA into *Escherichia coli* to express the polypeptide and to obtain the polypeptide in the resultant culture in a considerably high yield. These findings were disclosed in Japanese Patent Application Nos.184,162/94 and 304,203/94, filed by the present applicant. The present invention provides uses of the polypeptide as an agent for susceptive disease.

BRIEF DESCRIPTION OF THE
ACCOMPANYING DRAWINGS

FIG. 1 is a figure of the structure of recombinant DNA pKGFHH2.
KGFHH2 cDNA: cDNA encoding the present polypeptide
Ptac: tac promoter
rrnBT1T2: terminator of ribosome RNA operon
AmpR: ampicillin resistant gene
pBR322ori: replication initiation site of *Escherichia coli*.

DETAILED DESCRIPTION OF THE
INVENTION

In vivo present agent for susceptive diseases induces the IFN-γ production by human immunocompetent cells, and exerts a therapeutic and/or prophylactic effect on patients suffering from IFN-γ susceptive diseases when administered. When a polypeptide has an activity of enhancing the cytotoxicity of killer cells or of inducing the formation of killer cells, it exerts a strong effect in the treatment of serious diseases including malignant tumors.

The polypeptide used in the present invention has either the amino acid sequence of SEQ ID NO:1 (where the symbol "Xaa" represents "isoleucine" or "threonine") or its homologous amino acid sequences, and induces the IFN-γ production by immunocompetent cells. Examples of the homologous amino acid sequences include those which correspond to the amino acid sequence of SEQ ID NO:1 wherein one or more amino acids are replaced with other amino acids, to that wherein one or more amino acids are added to the N- and/or C-termini, and to that wherein one or more amino acids in the N- and/or C-termini are deleted. For example polypeptides such as, those isolated from natural sources by cell culture and those artificially synthesized by recombinant DNA technology and peptide synthesis, can be used in the present invention as long as they have either of these amino acid sequences and properties.

From an economical view point, recombinant DNA technology is advantageously used in the present invention. According to the technology, DNAs encoding those amino acid sequences are introduced into appropriate hosts derived from microorganisms and animals to obtain transformants which are then cultured in nutrient culture media in a conventional manner, and the resulting cultures are purified by conventional techniques used for purifying cytokines to obtain the objective polypeptide. Japanese Patent Application No.304,203/94, filed by the present applicant, discloses in detail the preparation of the polypeptide using recombinant DNA technology, and Japanese Patent Application No.58240/95, titled "Monoclonal antibody", filed by the present applicant on Feb. 23, 1995, discloses a purification method which can produce a polypeptide with the highest possible purity at the lowest possible labor- and material-costs.

As described above, the polypeptide has a property of inducing the IFN-γ production by immunocompetent cells. When administered to human, the present agent for susceptive diseases induces the IFN-γ production by immunocompetent cells in vivo, and exerts a satisfactory therapeutic and/or prophylactic effect on IFN-γ susceptive diseases. The polypeptide having the amino acid sequence of SEQ ID NO:1 has the properties of enhancing the cytotoxicity of killer cells such as NK cells, LAK cells (lymphokine-activating killer cells), cytotoxic T-cells, and inducing the formation of the killer cells, as well as the property of inducing the IFN-γ production by immunocompetent cells, so that the killer cells treat and/or prevent the polypeptide-susceptive diseases. Thus, the wording "susceptive diseases" as referred to in the present specification means diseases in general which include IFN-γ susceptive diseases and those which can be directly or indirectly treated and/or prevented by IFN-γs and/or killer cells: For example, viral diseases such as hepatitis, herpes syndrome, condyloma, and AIDS; bacterial diseases such as Candidiasis and malaria; solid malignant tumors such as renal cancer, mycosis fungoides, and chronic granulomatous disease; blood cell malignant tumors such as adult T cell leukemia, chronic myelogenous leukemia, and malignant leukemia; and immune diseases such as allergy and rheumatism. When the polypeptide is used along with interleukin 3, it exerts a strong effect on the treatment or the remission of leukemia and myeloma, as well as leukopenia and thrombopenia induced by radiations and chemotherapeutic agents to treat malignant tumors.

The present agent for susceptive diseases can be used widely in the treatment and/or the prevention of the above susceptive diseases as an antitumor agent, antiviral agent, antiseptic, immunotherapeutic agent, platelet-increasing agent, and leukocyte-increasing agent. Although it varies depending on the types of agents used for such purposes and the susceptive diseases to be treated, the present agent is generally processed into an agent in the form of a liquid, paste or solid which contains the polypeptide in an amount of 0.000001–100 w/w %, preferably, 0.0001–0.1 w/w %, on a dry solid basis (d.s.b.).

The present agent can be used intact or processed into compositions by mixing with a physiologically-acceptable carrier, adjuvant, excipient, diluent, and/or stabilizer, and, if necessary, further mixing with one or more other biologically-active substances such as interferon-α, interferon-β, interleukin 2, interleukin 3, interleukin 12, TNF-α, TNF-β, carboquone, cyclophosphamide, aclarubicin, thiotepa, busulfan, ancitabine, cytarabine, 5-fluorouracil, 5-fluoro-1-(tetrahydro-2-furyl)uracil, methotrexate, actinomycin D, chromomycin A3, daunorubicin, doxorubicin, bleomycin, mitomycin C, vincristine, vinblastine, L-asparaginase, radio gold colloidal, KRESTIN®, picibanil, lentinan, and Maruyama vaccine. Among these combinations, a composition consisting of the polypeptide and interleukin 2 is especially useful because interleukin 2 acts as a cofactor for the polypeptide when inducing the IFN-γ production by immunocompetent cells. The combination of the polypeptide and a natural or recombinant human interleukin 2 induces a prescribed level of IFN-γ production even when the sole use of the polypeptide could not substantially induce the IFN-γ production by immunocompetent cells. The use of a combination of the polypeptide and interleukin 12 induces a greater level of IFN-γ production that could not be readily attained by their respective use. Because the polypeptide increases the inhibitory activity of interleukin 12 on the production of immunoglobulin E antibody, the polypeptide can be used as an agent to treat atopies including allergic asthma, atopic bronchial asthma, hay fever, allergic rhinitis, atopic dermatitis, vascular edema, and atopic disorder of the digestive system. The sole administration of the polypeptide attains a desired therapeutic effect on humans because there inherently exists interleukin 12 in the human body, though the amount is slight.

The present agent for susceptive diseases includes those in a unit dose form meaning a physically separated and formed medicament suitable for administration, and contains the polypeptide in a daily dose or in a dose from ⅟₄₀ to several folds (up to 4 folds) of the daily dose. Examples of these medicaments are injections, liquids, powders, granules, tablets, capsules, sublinguals, ophthalmic solutions, nasal drops, and suppositories.

The agent for susceptive diseases can be orally or parenterally administered to patients, and as described below it can be used to activate antitumor cells in vitro. In both administrations, the agent exerts a satisfactory effect in the treatment and/or the prevention of susceptive diseases. Although it varies depending on the types of susceptive diseases and their symptoms, the agent can be orally administered to patients or parenterally administered to patients' intradermal tissues, subcutaneous tissues, muscles, and veins at a dose in the range of about 0.1–50 mg/shot, preferably, about one μg/shot to one mg/shot, 1–4 times/day or 1–5 times/week, for one day to one year.

The agent according to the present invention can be also used in so called "antitumor immunotherapy" using interleukin 2. Generally, the antitumor immunotherapy is roughly classified into (i) a method for directly administering interleukin 2 to the body of patients with malignant tumors, and (ii) a method for introducing antitumor cells activated in vitro by interleukin 2 (adoptive immunotherapy). The immunotherapeutic effect can be significantly enhanced when administered along with the polypeptide. In method (i), the polypeptide is administered to patients in an amount of about 0.1 μg/shot/adult to one mg/shot/adult at 1–10 times simultaneously or before the administration of interleukin 2. The dose of interleukin 2 is generally set to a dose in the range of about 10,000 to 1,000,000 units/shot/adult, though it varies depending on the types of malignant tumors, patients' symptoms, and the polypeptide dose. While in method (ii), mononuclear cells and lymphocytes, collected from patients with malignant tumors, are cultured in the presence of interleukin 2 and about one ng to one mg of the polypeptide per $1 \times 10^6$ cells of these blood cells. After culturing for a prescribed period of time, NK cells and LAK cells were collected from the culture, and introduced into the patients' body. Diseases which can be treated by the present antitumor immunotherapy are, for example, solid malignant tumors such as colonic cancer, rectal cancer, gastric cancer, thyroid carcinoma, cancer of the tongue, bladder carcinoma, choriocarcinoma, hepatoma, prostatic cancer, carcinoma uteri, laryngeal, lung cancer, breast cancer, malignant melanoma, Kaposi's sarcoma, cerebral tumor, neuroblastoma, tumor of the ovary, testicular tumor, osteosarcoma, cancer of the pancreas, renal cancer, hypernephroma, hemangioendothelioma, and blood cell malignant tumors such as leukemia and malignant lymphoma.

The following Experiments explain the preparation of the polypeptide by recombinant DNA technology, and the biological activity and toxicity:

Experiment 1
Preparation of Polypeptide
Experiment 1-1
Preparation of Transformant KGFHH2

To a 0.5-ml reaction tube were added 8 μl of 25 mM magnesium chloride, 10 μl of 10×PCR buffer, one μl of 25 mM dNTP mix, one μl of 2.5 units/μl of AmpliTaq DNA polymerase, one ng of a recombinant DNA containing the base sequence of SEQ ID NO:2 prepared from a phage DNA clone by the method in Japanese Patent Application No.304, 203/94 and containing a DNA encoding the polypeptide of SEQ ID NO:1, and an adequate amount of a sense primer and an antisense primer represented by 5'-ATAGAATTCAAATGTACTTTGGCAAGCTTGAATC-3' (SEQ ID NO:8), chemically synthesized based on an amino acid sequence near the N- and C-termini of SEQ ID NO:1, and 5'-ATAAAGCTTCTAGTCTTCGTTTTGAAC-3' (SEQ ID NO:9), and the mixture solution was admixed with sterilized distilled water to give a total volume of 100 μl. The mixture solution was in a conventional manner successively incubated at 94° C. for one min, at 43° C. for one min, and at 72° C. for one min, and this sequential incubation was repeated 3 times. The resultant mixture was further successively incubated at 94° C. for one min, at 60° C. for one min, and at 72° C. for one min, and this sequential incubation was repeated 40 times to effect PCR reaction.

The resultant PCR reaction mixture and "pCR-Script SK (+)", a plasmid vector commercialized by Stratagene Cloning Systems, California, USA, were ligated with DNA ligase to obtain a recombinant DNA which was then introduced with competent cell into "Escherichia coli XL-1 Blue MRF'Kan", a microorganism commercialized by Stratagene Cloning Systems, California, USA, to transform the microorganism. The transformant thus obtained was inoculated into L-broth (pH 7.2) containing 50 μg/ml ampicillin, and cultured at 37° C. for 18 hours under shaking conditions, followed by centrifuging the resultant culture to collect the proliferated transformants, and isolating recombinant DNAs with conventional alkaline-SDS method. A part of the recombinant DNAs was provided, analyzed by the dideoxy method, and revealed that it contained a DNA which has cleavage sites of Eco RI and Hind III at the 5'- and 3'-terminals of SEQ ID NO:2, a methionine codon which initiates the polypeptide synthesis and positions in the sites corresponding to those before and after the N- and C-termini of SEQ ID NO:2, and a TAG codon which terminates the polypeptide synthesis.

The remaining recombinant DNAs were cleaved with restriction enzymes Eco RI and Hind III, and 0.1 μg of the resultant Eco RI-Hind III DNA fragment obtained with "DNA LIGATION KIT Version 2", a DNA ligation kit commercialized by Takara Shuzo Co., Ltd., Tokyo, Japan, and 10 ng of "pKK223-3", a plasmid vector commercialized by Pharmacia LKB Biotechnology AB, Uppsala, Sweden, which had been previously cleaved with the above restriction enzymes, were ligated by incubating them at 16° C. for 30 min to obtain a replicable recombinant DNA "pKGFHH2". By using a competent cell method, Escherichia coli Y1090 strain (ATCC 37197) was transformed with the replicable recombinant DNA pKGFHH2, and the formed transformant "KGFHH2" was inoculated into L-broth (pH 7.2) containing 50 μ/ml ampicillin, and incubated at 37° C. for 18 hours under shaking conditions. The resultant culture was centrifuged to collect the proliferated transformants, and a portion of which was treated with conventional SDS-alkaline method to extract the recombinant DNA pKGFHH2. As is shown in FIG. 1, the analysis by the dideoxy method revealed that, in the recombinant DNA pKGFHH2, the KGFHH2 cDNA, which contains the base sequence of SEQ ID NO:2 (where the amino acid sequence corresponding to SEQ ID NO:1 and encoded by SEQ ID NO:2 is presented below the base sequence), was ligated to the downstream of a Tac promoter.

```
SEQ ID NO:2:

TAC TTT GGC AAG CTT GAA TCT AAA TTA TCA GTC ATA AGA AAT TTG AAT    48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT    96
Asp Gln Val Leu Phe Ile Asp Gln Gly Asn Arg Pro Leu Phe Glu Asp
                20                  25                  30

ATG ACT GAT TCT GAC TGT AGA GAT AAT GCA CCC CGG ACC ATA TTT ATT   144
Met Thr Asp Ser Asp Cys Arg Asp Asn Ala Pro Arg Thr Ile Phe Ile
                35                  40                  45

ATA AGT ATG TAT AAA GAT AGC CAG CCT AGA GGT ATG GCT GTA ACT ATC   192
```

-continued

```
                Ile Ser Met Tyr Lys Asp Ser Gln Pro Arg Gly Met Ala Val Thr Ile
                    50              55              60

TCT GTG AAG TGT GAG AAA ATT TCA AYT CTC TCC TGT GAG AAC AAA ATT        240
Ser Val Lys Cys Glu Lys Ile Ser Xaa Leu Ser Cys Glu Asn Lys Ile
65              70              75              80

ATT TCC TTT AAG GAA ATG AAT CCT CCT GAT AAC ATC AAG GAT ACA AAA        288
Ile Ser Phe Lys Glu Met Asn Pro Pro Asp Asn Ile Lys Asp Thr Lys
                85              90              95

AGT GAC ATC ATA TTC TTT CAG AGA AGT GTC CCA GGA CAT GAT AAT AAG        336
Ser Asp Ile Ile Phe Phe Gln Arg Ser Val Pro Gly His Asp Asn Lys
            100             105             110

ATG CAA TTT GAA TCT TCA TCA TAC GAA GGA TAC TTT CTA GCT TGT GAA        384
Met Gln Phe Glu Ser Ser Ser Tyr Glu Gly Tyr Phe Leu Ala Cys Glu
        115             120             125

AAA GAG AGA GAC CTT TTT AAA CTC ATT TTG AAA AAA GAG GAT GAA TTG        432
Lys Glu Arg Asp Leu Phe Lys Leu Ile Leu Lys Lys Glu Asp Glu Leu
    130             135             140

GGG GAT AGA TCT ATA ATG TTC ACT GTT CAA AAC GAA GAC                    471
Gly Asp Arg Ser Ile Met Phe Thr Val Gln Asn Glu Asp
145             150             155
```

Experiment 1-2
Production and Purification of Polypeptide from Transformant KGFHH2

An L-broth (pH 7.2) containing 50 μg/ml of ampicillin was sterilized by autoclaving, cooled to 37° C., inoculated with the transformant KGFHH2 in Experiment 1-1, and incubated at the same temperature for 18 hours under shaking conditions to obtain a seed culture. An eighteen L of a fresh preparation of the same L-broth was placed in a 20-L jar fermenter, sterilized similarly as above, cooled to 37° C., inoculated with one v/v % of the seed culture, and cultured at the same temperature for 8 hours under aeration and agitation conditions. The resultant culture was centrifuged to collect cells which were then suspended in a mixture solution (pH 7.3) consisting of 150 mM sodium chloride, 16 mM disodium hydrogen phosphate, and 4 mM sodium dihydrogen phosphate, disrupted with ultrasonic, and centrifuged to remove cell debris to obtain a supernatant.

Ammonium sulfate was added to the supernatant to give a concentration of 40 w/v %, dissolved to homogeneity, and the solution was centrifuged to obtain a supernatant. The supernatant was first mixed with 150 mM phosphate buffer (pH 6.6) containing 1.5 M ammonium sulfate, and then fed to a column packed with "PHENYL SEPHAROSE", a product of Pharmacia LKB Biotechnology AB, Uppsala, Sweden, which had been previously equilibrated with 10 mM phosphate buffer (pH 6.6) containing 1.5 M ammonium sulfate, followed by washing the column with a fresh preparation of the same buffer, and feeding to the column a gradient buffer of ammonium sulfate ranging from 1.5 M to 0 M in 10 mM phosphate buffer (pH 6.6).

According to the method as disclosed in Japanese Patent Application No. 58240/95, titled "Monoclonal antibody" applied by the present applicant on Feb. 23, 1995, a gel for immunoaffinity chromatography was prepared and packed in a plastic cylindrical column which was then washed with phosphate buffered saline (hereinafter abbreviated as "PBS"), fed with 10 ml of the fractions eluted from the PHENYL SEPHAROSE column at about 1.0 M ammonium sulfate in the above column chromatography, washed with a fresh preparation of the same PBS, and fed with 0.1 M glycine-HCl buffer (pH 2.5) containing one M sodium chloride, followed by collecting fractions with IFN-γ inducibility. The fractions were pooled, dialyzed against PBS at 4° C. overnight, and concentrated, followed by assaying the resultant concentrate for IFN-γ inducibility and protein content, which revealed that the purification procedure yielded about 25 mg of the polypeptide with a purity at least 95% per one L of culture.

Analysis according to the method in Japanese Patent Application No. 304,203/94 revealed that the purified polypeptide had the following physicochemical properties: When electrophoresed in SDS-polyacrylamide gel under reducing conditions, the purified protein appeared as a main protein band having IFN-γ inducibility at a position corresponding to 18,500±3,000 daltons, while giving a pI of 4.9±1.0 on chromatofocusing. The amino acid sequence containing the N-terminus of the purified protein has the amino acid sequence of SEQ ID NO:3 which is the same as that of SEQ ID NO:1 where methionine is linked to the N-terminus.

```
SEQ ID NO:3:
Met Tyr Phe Gly Lys Leu Glu Ser Lys Leu Ser
1               5                   10
```

Experiment 2
Biological Activity
Experiment 2-1
Production of IFN-γ by Immunocompetent Cell Fresh blood was collected from healthy volunteers with heparinized syringes, and diluted with serum-free RPMI 1640 medium (pH 7.4) by 2 folds. The diluted blood was overlaid on Ficoll and centrifuged to obtain lymphocytes which were then washed with RPMI 1640 medium (pH 7.4) supplemented with 10 v/v % fetal calf serum, and suspended in a fresh preparation of the same medium to give a cell density of 5×10⁶ cells/ml. The cell suspension was distributed to 96-well microplates in an amount of 0.15 ml/well.

A polypeptide obtained by the method in Experiment 1-2 was diluted to give an appropriate concentration with RPMI 1640 medium (pH 7.4) supplemented with 10 v/v % fetal calf serum, and the diluted solution was distributed to the microplates in an amount of 0.05 ml/well, followed by adding to the microplates 0.05 ml/well of a fresh preparation of the same medium supplemented with or without 2.5 µg/ml of concanavalin A or 50 units/ml of a recombinant human interleukin 2, and then incubating the microplates at 37° C. for 24 hours in an incubator under 5 v/v % $CO_2$ conditions. After cultivation, 0.1 ml of culture supernatant in each well was sampled and assayed for IFN-γ content with conventional enzyme immunoassay. As a control, a system free of the polypeptide was provided, and similarly treated as above. The results are presented in Table 1. In the Table, the IFN-γ content was calibrated using Gg23-901-530, an International Standard for Interferon, Human (HuIFN-γ), obtained from National Institute of Health, Bethesda, Md., USA, and expressed by international units (IU).

TABLE 1

| Polypeptide concentration (ng/ml) | Polypeptide | Polypeptide plus 0.5 µg/ml of concanavalin A | Polypeptide plus 10 U/ml of interleukin 2 |
|---|---|---|---|
| 0 | 0 | 0 | 0 |
| 1.6 | 1 ± 2 | 92 ± 32 | 184 ± 12 |
| 8.0 | 3 ± 1 | 220 ± 21 | 397 ± 31 |
| 40.0 | 6 ± 4 | 380 ± 34 | 526 ± 28 |
| 200.0 | 14 ± 6 | 549 ± 105 | 637 ± 99 |

IFN-γ productivity (IU/ml)

The results in Table 1 show that lymphocytes as immunocompetent cells produced IFN-γ when the polypeptide acts on them. As is evident from the results, the combination use of the polypeptide and interleukin 2 or concanavalin A as a cofactor enhanced IFN-γ production.

Experiment 2-2
Enhancement of Cytotoxicity by NK Cell

Fresh blood was collected from healthy volunteers with heparinized syringes, and diluted 2 fold with 10 mM phosphate buffer (pH 7.4) containing 140 mM sodium chloride. The blood was overlaid on PERCOLL, centrifuged, and further subjected to PERCOLL gradient centrifugation to obtain high-density lymphocytes.

The lymphocytes were suspended in RPMI 1640 medium (pH 7.2) containing 10 µg/ml kanamycin, $5×10^{-5}$ M 2-mercaptoethanol, and 10 v/v % fetal calf serum to give a cell density of $1×10^6$ cells/ml, and the suspension was distributed into 12-well microplates in an amount of 0.5 ml/well. A polypeptide obtained by the method in Experiment 1-2 was appropriately diluted with a fresh preparation of the same medium, and the diluted solution was distributed to the microplates in an amount of 1.5 ml/well, followed by distributing to the microplates 0.5 ml/well of a fresh preparation of the same medium with or without 50 units/ml of a recombinant human interleukin 2, incubating the microplates in an incubator at 37° C. for 24 hours under 5 v/v % $CO_2$ conditions, and washing the microplates with 10 mM phosphate buffer (pH 7.4) containing 140 mM sodium chloride to obtain cultured lymphocytes containing NK cells as effector cells. K-562 Cells (ATCC CCL 243), derived from human chronic myelogenous leukemia, as an NK cell-susceptive target cells which were labelled in the usual manner with $^{51}$Cr, were distributed to 96-well microplates to give $1×10^4$ cells/well, and the effector cells were added to each well in the ratio ((effector cells):(target cells)) of 2.5:1, 5:1 or 10:1, and incubated in an incubator at 37° C. for 4 hours under 5 v/v % $CO_2$ conditions. According to a conventional method, the radioactivity of each supernatant in each well was measured to count the dead target cells. In each system, the percentage (%) of the dead target cells to the target cells was calculated to determine the cytotoxicity level. The results are presented in Table 2.

TABLE 2

| Concentration of polypeptide (pM*) | Concentration of interleukin 2 (unit/ml) | Cytotoxicity (%) (Effector cell):(Target cell) | | |
|---|---|---|---|---|
| | | 2.5:1 | 5:1 | 10:1 |
| 0 | 0 | 22 | 35 | 65 |
| 0 | 10 | 30 | 48 | 73 |
| 0.5 | 0 | 23 | 36 | 66 |
| 0.5 | 10 | 32 | 50 | 75 |
| 5 | 0 | 25 | 39 | 68 |
| 5 | 10 | 35 | 52 | 78 |
| 50 | 0 | 29 | 47 | 73 |
| 50 | 10 | 41 | 59 | 85 |
| 500 | 0 | 37 | 50 | 83 |
| 500 | 10 | 52 | 70 | 93 |

Note : *In the Table, the symbol "pM" means $10^{-12}$ M.

The results in Table 2 show that the polypeptide has an activity of enhancing the cytotoxicity by NK cells. As is shown in Table 2, the coexistence of interleukin 2 further enhances the cytotoxicity.

Experiment 2-3
Induction of LAK Cell Formation

According to what is done conventionally, $^{51}$Cr-labelled Raji cells (ATCC CCL 86), derived from human Burkitt lymphoma as a target cell non-susceptive to NK cells, were placed in 96-well microplates to give $1×10^4$ cells/well, and cultured for 72 hours. Cultured lymphocytes, containing LAK cells as effector cells prepared similarly as in Experiment 2-2, and target cells were added to the microplates in the ratio of 5:1, 10:1 or 20:1, and the microplates were incubated in an incubator at 37° C. for 4 hours under 5 v/v % $CO_2$ conditions. Thereafter, the radioactivity of each supernatant in each well was measured, and the cytotoxicity (%) was calculated similarly as in Experiment 2-2. The results are presented in Table 3.

TABLE 3

| Concentration of polypeptide (pM*) | Concentration of interleukin 2 (unit/ml) | Cytotoxicity (%) (Effector cell):(Target cell) | | |
|---|---|---|---|---|
| | | 5:1 | 10:1 | 20:1 |
| 0 | 0 | 11 | 21 | 34 |
| 0 | 10 | 15 | 28 | 38 |
| 0.5 | 0 | 13 | 22 | 35 |
| 0.5 | 10 | 17 | 31 | 43 |
| 5 | 0 | 15 | 23 | 39 |
| 5 | 10 | 19 | 34 | 48 |
| 50 | 0 | 20 | 25 | 44 |
| 50 | 10 | 23 | 42 | 54 |
| 500 | 0 | 27 | 34 | 57 |
| 500 | 10 | 31 | 54 | 67 |

Note : *In the Table, the symbol "pM" means $10^{-12}$ M.

The results in Table 3 show that the polypeptide has an activity of inducing the formation of LAK cells. As is shown in the results, the coexistence of interleukin 2 further enhances the induction.

Experiment 3

Acute Toxicity Test

According to what is done conventionally, a purified polypeptide obtained by the method in Experiment 1-2 was percutaneously, perorally or intraperitoneally administered to 8-week-old mice. As a result, the $LD_{50}$ of the purified polypeptide was about one mg/kg or higher and independent of the administration routes. This evidences that the polypeptide can be safely incorporated into pharmaceuticals for administering human.

As is well known, IFN-γs closely relate to human biophylaxis through their infectious protection against bacteria, growth inhibitory activity for malignant tumors, immunoregulatory activity, and production inhibitory activity on immunoglobulin E antibody.

As is described above, the IFN-γs have been developed as an agent for human susceptive diseases, and diseases to be treated, and their doses, administration routes, and safeness were almost studied. As is described in "*Cytokines in Cancer Therapy*", edited by Frances R. Balkwill, translated by Yoshihiko WATANABE (1991), published by Tokyo-Kagaku-Dojin, Tokyo, Japan, it is reported that almost satisfactory results were obtained when the treatment using killer cells such as NK cells and LAK cells was applied on a variety of human diseases including antitumor immunotherapy. Recently, it is noted that there is a relationship between the therapeutic effect and the induction of killer cells or the enhancement of the cytotoxicity by killer cells using cytokines. For example, T. FUJIOKA reported in "*British Journal of Urology*", Vol.73, No.1, pp.23–31 (1994) that, in the antitumor immunotherapy using LAK cells and interleukin 2, interleukin 2 strongly induced LAK cell formation and exerted a remarkable cancer metastasis-inhibitory activity on human cancers without inducing serious side effects.

Thus, it is revealed that IFN-γs and killer cells deeply relate to the treatment and/or prevention of a variety of human diseases, and greatly contribute to their complete treatment or remission. In these circumstances, and as is evident from the results in Experiments 2 and 3, the polypeptide induces the IFN-γ production by immunocompetent cells, and enhances the cytotoxicity by NK cells or induces the formation of LAK cells without causing serious side effects. These facts show that the present susceptive diseases can be repeatedly administered to humans without inducing serious side effects, and exerted a satisfactory effect in the treatment and/or the prevention of diseases closely relating to IFN-γs and killer cells.

The following Examples explain the present agent for susceptive diseases:

EXAMPLE 1

Solution

A polypeptide, obtained by the method in Experiment 1-2, was dissolved in physiological saline containing one w/v % human serum albumin as a stabilizer to obtain a one mg/ml polypeptide solution which was then sterilized by membrane filter to obtain a solution.

The product with a satisfactory stability can be used as an injection, ophthalmic solution, and collunarium in the treatment and/or the prevention of susceptive diseases such as malignant tumors, viral diseases, bacterial infectious diseases, and immune diseases.

EXAMPLE 2

Dry Injection

A polypeptide, obtained by the method in Experiment 1-2, was dissolved in 100 ml physiological saline containing one w/v % purified gelatin as a stabilizer, and the solution was in the usual manner sterilized with a membrane filter. One ml aliquots of the sterilized solution were distributed to vials, lyophilized, and cap sealed.

The product with a satisfactory stability can be used as a dry injection for treating and/or preventing susceptive diseases such as malignant tumors, viral diseases, bacterial diseases, and immune diseases.

EXAMPLE 3

Ointment

"HI-BIS-WAKO 104", a carboxyvinylpolymer commercialized by Wako Pure Chemicals, Tokyo, Japan, and a purified trehalose were dissolved in distilled water to give concentrations of 1.4 w/w % and 2.0 w/w %, respectively, and a polypeptide obtained by the method in Experiment 1-2 was dissolved to homogeneity in the solution, followed by adjusting the pH of the resultant solution to pH 7.2 to obtain a paste containing about one mg/g of the polypeptide.

The product with a satisfactory spreadability and stability can be used as an ointment for treating and/or preventing susceptive diseases such as malignant tumors, viral diseases, bacterial infectious diseases, and immune diseases.

EXAMPLE 4

Tablet

A polypeptide, obtained by the method in Experiment 1-2, and LUMIN, i.e. [bis-4-(1-ethylquinoline)][γ-4'-(1-ehtylquinoline] pentamethionine cyanine, as a cell activator were mixed to homogeneity with "FINETOSE®", an anhydrous crystalline α-maltose commercialized by Hayashibara Co., Ltd., Okayama, Japan, and the mixture was in usual manner tabletted by a tabletting machine to obtain tablets, about 200 mg weight each, containing the polypeptide and the LUMIN, about one mg each.

The product, having a satisfactory swallowing ability, stability, and cell activating activity, can be used as a tablet for treating and/or preventing susceptive diseases such as malignant tumors, viral diseases, bacterial infectious diseases, and immune diseases.

EXAMPLE 5

Adoptive Immunotherapeutic Agent

Mononuclear cells were isolated from peripheral blood of a patient with malignant lymphoma, suspended in RPMI 1640 medium (pH 7.2) which was supplemented with 10 v/v % human AB serum and preheated to 37° C. to give a cell density of about $1\times10^6$ cells/ml, and mixed with about 1.0 μg/ml of a polypeptide, obtained by the method in Experiment 1-2, and about 100 units/ml of a recombinant human interleukin 2, followed by incubating the resultant in a 5 v/v % $CO_2$ incubator at 37° C. for one week, and centrifuging the resultant culture to collect LAK cells.

The LAK cells thus obtained exhibit a strong cytotoxicity on lymphoma cells when introduced into the donor patient, and exert a higher cytotoxicity than that attained by the adoptive immunotherapy using interleukin 2 alone. Cytotoxic T-cells, obtained by similarly treating lymphocytes invaded into tumor tissues from the patient, in place of the above lymphocytes, was injected into the donor patient and resulting in an exertion of the similar effect attained by the LAK cells. The adoptive immunotherapeutic agent can be arbitrarily used to treat solid malignant tumors such as renal cancer, malignant melanoma, colonic cancer, rectal cancer, and lung caner.

As is described above, the present agent for susceptive diseases exerts a satisfactory effect in the treatment and/or the prevention of susceptive diseases such as malignant tumors, viral diseases, bacterial infectious diseases, and immune diseases. Furthermore, the present agent which contains a polypeptide having an activity of enhancing the cytotoxicity by killer cells or inducing the formation of killer cells exert a significant effect in the treatment of serious diseases such as malignant tumors.

The present invention with these significant functions and effects is a significant invention which greatly contributes to this field.

While there has been described what is at present considered to be the preferred embodiments of the invention, it will be understood the various modifications may be made therein, and it is intended to cover in the appended claims all such modifications as fall within the true spirit and scope of the invention.

We claim:

1. A pharmaceutical composition for inducing human IFN-γ, enhancing cytotoxicity of human killer cells or inducing formation of human killer cells, comprising a pharmaceutically acceptable carrier, and as an effective ingredient, 0.000001 w/w % to 100 w/w % on a dry solid basis of a polypeptide of SEQ ID NO:1, where amino acid residue 73 of SEQ ID NO:1, as represented by Xaa, is Ile or Thr, or a homologous polypeptide thereof, wherein the polypeptide and the homologous polypeptide thereof has the following physicochemical properties:

(a) an amino acid sequence selected from the group consisting of SEQ ID NO:1, where amino acid residue 73, as represented by Xaa, is Ile or Thr, and a homologous sequence thereof where one amino acid residue in SEQ ID NO:1 is replaced with a different amino acid, or one amino acid residue is added to or deleted from the N-terminus or the C-terminus of SEQ ID NO:1, wherein said homologous polypeptide has substantially the same physicochemical properties and biological activity as the polypeptide of SEQ ID NO:1;

(b) Molecular weight 18,500±3,000 daltons on sodium dodecyl sulfate polyacrylamide gel electrophoresis (SDS-PAGE);

(c) Isoelectric point (pI) 4.9±1.0 on chromatofocusing;

(d) Biological activity Inducing IFN-γ production by human immunocompetent cells; and (d) Acute toxicity Having an $LD_{50}$ of at least about one mg/kg when tested in mice.

2. The pharmaceutical composition according to claim 1, wherein said effective ingredient is the polypeptide of SEQ ID NO:1, where amino acid residue 73, as represented by Xaa, is Ile or Thr.

3. The pharmaceutical composition according to claim 2, further comprising at least one member selected from the group consisting of stabilizer, adjuvants, excipients, diluents, and biologically-active substances.

4. The pharmaceutical composition according to claim 3, wherein said stabilizer is at least one member selected from the group consisting of serum albumin, gelatin, maltose, and trehalose.

5. The pharmaceutical composition according to claim 3, wherein said biologically-active substance is at least one member selected form the group consisting of interleukins, interferons, tumor necrosis factors, and antitumor agents.

6. The pharmaceutical composition according to claim 1, wherein said effective ingredient is the homologous polypeptide.

7. The pharmaceutical composition according to claim 6, further comprising at least one member selected from the group consisting of interleukin 2 and concanavalin A.

8. The pharmaceutical composition according to claim 1, wherein the killer cells are selected from the group consisting of natural killer cells, lymphokine-activating killer cells, and cytotoxic T-cells.

9. The pharmaceutical composition according to claim 6, further comprising a stabilizer selected from the group consisting of serum albumin, gelatin, maltose, and trehalose.

* * * * *

```
                           SEQUENCE LISTING (1) GENERAL INFORMATION:

(iii) NUMBER OF SEQUENCES:9

(2) INFORMATION FOR SEQ ID NO:1:

(i) SEQUENCE CHARACTERISTICS:
           (A) LENGTH:157 amino acids
           (B) TYPE:amino acid
           (D) TOPOLOGY:linear (ii) MOLECULE TYPE:peptide (xi) SEQUENCE DESCRIPTION:SEQ ID NO:1:

Tyr Phe Gly Lys Leu Glu Ser Lys Leu Ser Val Ile Arg Asn Leu Asn
   1               5                   10                  15

Asp Gln Val Leu Phe Ile Asp Gln Gly Asn Arg Pro Leu Phe Glu Asp
                   20                  25                  30

Met Thr Asp Ser Asp Cys Arg Asp Asn Ala Pro Arg Thr Ile Phe Ile
               35                  40                  45

Ile Ser Met Tyr Lys Asp Ser Gln Pro Arg Gly Met Ala Val Thr Ile
       50                  55                  60

Ser Val Lys Cys Glu Lys Ile Ser Xaa Leu Ser Cys Glu Asn Lys Ile
   65                  70                  75                  80

Ile Ser Phe Lys Glu Met Asn Pro Pro Asp Asn Ile Lys Asp Thr Lys
                   85                  90                  95

Ser Asp Ile Ile Phe Phe Gln Arg Ser Val Pro Gly His Asp Asn Lys
                   100                 105                 110

Met Gln Phe Glu Ser Ser Ser Tyr Glu Gly Tyr Phe Leu Ala Cys Glu
               115                 120                 125

Lys Glu Arg Asp Leu Phe Lys Leu Ile Leu Lys Lys Glu Asp Glu Leu
               130                 135                 140

Gly Asp Arg Ser Ile Met Phe Thr Val Gln Asn Glu Asp
   145                 150                 155

(2) INFORMATION FOR SEQ ID NO:2:

(i) SEQUENCE CHARACTERISTICS:
           (A) LENGTH:471 base pairs
           (B) TYPE:nucleic acid
           (C) STRANDEDNESS:double
           (D) TOPOLOGY:linear (ii) MOLECULE TYPE:cDNA to mRNA
```

(vi) ORIGINAL SOURCE:
             (A) ORGANISM:human
             (B) INDIVIDUAL ISOLATE:liver (ix) FEATURE:
             (A) NAME/KEY:mat peptide
             (B) LOCATION:1..471
             (C) IDENTIFICATION METHOD:S (xi) SEQUENCE DESCRIPTION:SEQ ID NO:2:

```
TAC TTT GGC AAG CTT GAA TCT AAA TTA TCA GTC ATA AGA AAT TTG AAT      48
Tyr Phe Gly Lys Leu Glu Ser Lys Leu Ser Val Ile Arg Asn Leu Asn
1               5                  10                  15

GAC CAA GTT CTC TTC ATT GAC CAA GGA AAT CGG CCT CTA TTT GAA GAT      96
Asp Gln Val Leu Phe Ile Asp Gln Gly Asn Arg Pro Leu Phe Glu Asp
             20                  25                  30

ATG ACT GAT TCT GAC TGT AGA GAT AAT GCA CCC CGG ACC ATA TTT ATT     144
Met Thr Asp Ser Asp Cys Arg Asp Asn Ala Pro Arg Thr Ile Phe Ile
         35                  40                  45

ATA AGT ATG TAT AAA GAT AGC CAG CCT AGA GGT ATG GCT GTA ACT ATC     192
Ile Ser Met Tyr Lys Asp Ser Gln Pro Arg Gly Met Ala Val Thr Ile
     50                  55                  60

TCT GTG AAG TGT GAG AAA ATT TCA AYT CTC TCC TGT GAG AAC AAA ATT     240
Ser Val Lys Cys Glu Lys Ile Ser Xaa Leu Ser Cys Glu Asn Lys Ile
65                  70                  75                  80

ATT TCC TTT AAG GAA ATG AAT CCT CCT GAT AAC ATC AAG GAT ACA AAA     288
Ile Ser Phe Lys Glu Met Asn Pro Pro Asp Asn Ile Lys Asp Thr Lys
                 85                  90                  95

AGT GAC ATC ATA TTC TTT CAG AGA AGT GTC CCA GGA CAT GAT AAT AAG     336
Ser Asp Ile Ile Phe Phe Gln Arg Ser Val Pro Gly His Asp Asn Lys
             100                 105                 110

ATG CAA TTT GAA TCT TCA TCA TAC GAA GGA TAC TTT CTA GCT TGT GAA     384
Met Gln Phe Glu Ser Ser Ser Tyr Glu Gly Tyr Phe Leu Ala Cys Glu
         115                 120                 125

AAA GAG AGA GAC CTT TTT AAA CTC ATT TTG AAA AAA GAG GAT GAA TTG     432
Lys Glu Arg Asp Leu Phe Lys Leu Ile Leu Lys Lys Glu Asp Glu Leu
     130                 135                 140

GGG GAT AGA TCT ATA ATG TTC ACT GTT CAA AAC GAA GAC                 471
Gly Asp Arg Ser Ile Met Phe Thr Val Gln Asn Glu Asp
145                 150                 155
```

(2) INFORMATION FOR SEQ ID NO:3:

(i) SEQUENCE CHARACTERISTICS:
             (A) LENGTH:11
             (B) TYPE:amino acid
             (D) TOPOLOGY:linear (ii) MOLECULE TYPE:peptide (v) FRAGMENT TYPE:N-terminal fragment (xi) SEQUENCE DESCRIPTION:SEQ ID NO:3:

```
Met Tyr Phe Gly Lys Leu Glu Ser Lys Leu Ser
1               5                  10
```

(2) INFORMATION FOR SEQ ID NO:4:

(i) SEQUENCE CHARACTERISTICS:
             (A) LENGTH:25
             (B) TYPE:amino acid
             (D) TOPOLOGY:linear (ii) MOLECULE TYPE:peptide (v) FRAGMENT TYPE:internal fragment (xi) SEQUENCE DESCRIPTION:SEQ ID NO:4:

```
Ile Ile Ser Phe Glu Glu Met Asp Pro Pro Glu Asn Ile Asp Asp Ile
1               5                   10                  15
Gln Ser Asp Leu Ile Phe Phe Gln Lys
            20              25
```

(2) INFORMATION FOR SEQ ID NO:5:

(i) SEQUENCE CHARACTERISTICS:
        (A) LENGTH:18
        (B) TYPE:amino acid
        (D) TOPOLOGY:linear (ii) MOLECULE TYPE:peptide (v) FRAGMENT TYPE:internal fragment (xi) SEQUENCE DESCRIPTION:SEQ ID NO:5:

```
Gln Pro Val Phe Glu Asp Met Thr Asp Ile Asp Gln Ser Ala Ser Glu
1               5                   10                  15
Pro Gln
```

(2) INFORMATION FOR SEQ ID NO:6:

(i) SEQUENCE CHARACTERISTICS:
        (A) LENGTH:471 base pairs
        (B) TYPE:nucleic acid
        (C) STRANDEDNESS:double
        (D) TOPOLOGY:linear (ii) MOLECULE TYPE:cDNA to mRNA (vi) ORIGINAL SOURCE:
        (A) ORGANISM:mouse
        (B) INDIVIDUAL ISOLATE:liver (ix) FEATURE:
        (A) NAME/KEY:mat peptide
        (B) LOCATION:1..471
        (C) IDENTIFICATION METHOD:S (xi) SEQUENCE DESCRIPTION:SEQ ID NO:6:

```
AAC TTT GGC CGA CTT CAC TGT ACA ACC GCA GTA ATA CGG AAT ATA AAT     48
Asn Phe Gly Arg Leu His Cys Thr Thr Ala Val Ile Arg Asn Ile Asn
1               5                   10                  15

GAC CAA GTT CTC TTC GTT GAC AAA AGA CAG CCT GTG TTC GAG GAT ATG     96
Asp Gln Val Leu Phe Val Asp Lys Arg Gln Pro Val Phe Glu Asp Met
                20                  25                  30

ACT GAT ATT GAT CAA AGT GCC AGT GAA CCC CAG ACC AGA CTG ATA ATA    144
Thr Asp Ile Asp Gln Ser Ala Ser Glu Pro Gln Thr Arg Leu Ile Ile
            35                  40                  45

TAC ATG TAC AAA GAC AGT GAA GTA AGA GGA CTG GCT GTG ACC CTC TCT    192
Tyr Met Tyr Lys Asp Ser Glu Val Arg Gly Leu Ala Val Thr Leu Ser
        50                  55                  60

GTG AAG GAT AGT AAA AYG TCT ACC CTC TCC TGT AAG AAC AAG ATC ATT    240
Val Lys Asp Ser Lys Xaa Ser Thr Leu Ser Cys Lys Asn Lys Ile Ile
65                  70                  75                  80

TCC TTT GAG GAA ATG GAT CCA CCT GAA AAT ATT GAT GAT ATA CAA AGT    288
Ser Phe Glu Glu Met Asp Pro Pro Glu Asn Ile Asp Asp Ile Gln Ser
                85                  90                  95

GAT CTC ATA TTC TTT CAG AAA CGT GTT CCA GGA CAC AAC AAG ATG GAG    336
Asp Leu Ile Phe Phe Gln Lys Arg Val Pro Gly His Asn Lys Met Glu
            100                 105                 110
```

```
TTT GAA TCT TCA CTG TAT GAA GGA CAC TTT CTT GCT TGC CAA AAG GAA      384
Phe Glu Ser Ser Leu Tyr Glu Gly His Phe Leu Ala Cys Gln Lys Glu
            115                 120                 125

GAT GAT GCT TTC AAA CTC ATT CTG AAA AAA AAG GAT GAA AAT GGG GAT      432
Asp Asp Ala Phe Lys Leu Ile Leu Lys Lys Lys Asp Glu Asn Gly Asp
130                 135                 140

AAA TCT GTA ATG TTC ACT CTC ACT AAC TTA CAT CAA AGT                  471
Lys Ser Val Met Phe Thr Leu Thr Asn Leu His Gln Ser
145                 150                 155
```

(2) INFORMATION FOR SEQ ID NO:7:

(i) SEQUENCE CHARACTERISTICS:
        (A) LENGTH:157 amino acids
        (B) TYPE:amino acid
        (D) TOPOLOGY:linear (ii) MOLECULE TYPE:peptide (vi) ORIGINAL SOURCE:
        (A) ORGANISM:mouse
        (B) INDIVIDUAL ISOLATE:liver (xi) SEQUENCE DESCRIPTION:SEQ ID NO:7:

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
                20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
50                  55                  60

Val Lys Asp Ser Lys Xaa Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Lys Asp Glu Asn Gly Asp
130                 135                 140

Lys Ser Val Met Phe Thr Leu Thr Asn Leu His Gln Ser
145                 150                 155
```

(2) INFORMATION FOR SEQ ID NO:8:

(i) SEQUENCE CHARACTERISTICS:
        (A) LENGTH:34 base pairs
        (B) TYPE:nucleic acid
        (C) STRANDEDNESS:double
        (D) TOPOLOGY:linear (ii) MOLECULE TYPE:cDNA to mRNA (xi) SEQUENCE DESCRIPTION:SEQ ID NO:8:

```
ATAGAATTCA AATGTACTTT GGCAAGCTTG AATC                                34
```

(2) INFORMATION FOR SEQ ID NO:9:

(i) SEQUENCE CHARACTERISTICS:
        (A) LENGTH:27 base pairs
        (B) TYPE:nucleic acid

```
        (C) STRANDEDNESS:double
        (D) TOPOLOGY:linear (ii) MOLECULE TYPE:cDNA to mRNA (xi) SEQUENCE DESCRIPTION:SEQ ID NO:9:

ATAAAGCTTC TAGTCTTCGT TTTGAAC                                              27
```